United States Patent [19]

Radisson

[11] Patent Number: 5,347,001
[45] Date of Patent: Sep. 13, 1994

[54] PROCESS FOR PREPARING SULPHONYLPRISTINAMYCIN $II_B$

[75] Inventor: Xavier Radisson, Lyon, France

[73] Assignee: Rhone-Poulenc Rorer S.A., Antony, France

[21] Appl. No.: 961,915

[22] PCT Filed: Jul. 15, 1991

[86] PCT No.: PCT/FR91/00579
§ 371 Date: Jan. 4, 1993
§ 102(e) Date: Jan. 4, 1993

[87] PCT Pub. No.: WO92/01692
PCT Pub. Date: Feb. 6, 1992

[30] Foreign Application Priority Data

Jul. 16, 1990 [FR] France ............... 90 09033

[51] Int. Cl.$^5$ ............... C07D 498/14; C07K 5/12; A61K 31/42
[52] U.S. Cl. ............... 540/456; 540/455; 530/317
[58] Field of Search ............... 540/455, 456

[56] References Cited

U.S. PATENT DOCUMENTS 4,866,172 9/1988 Chatterjee et al. .......... 540/456

FOREIGN PATENT DOCUMENTS 322800 7/1989 European Pat. Off. .......... 540/456
2576022 7/1986 France .......... 540/456
2206577 1/1989 United Kingdom .......... 540/546

OTHER PUBLICATIONS

European Search Report.

Primary Examiner—Robert T. Bond
Attorney, Agent, or Firm—Morgan & Finnegan

[57] ABSTRACT

Method for preparing (dialkylamino-2 alkyl)sulphonyl-26 pristinamycin $II_B$ having general formula (I)

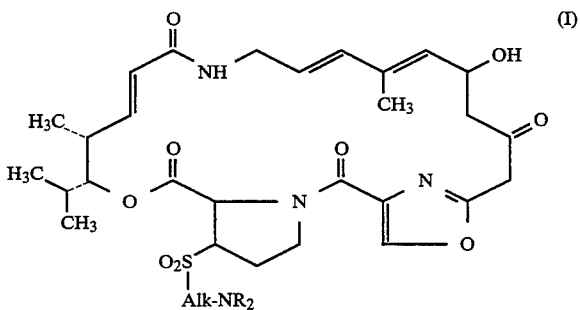

by oxidation of (dialkylamino-2 alkyl)thio-26 pristinamycin $II_B$ with 3,5 to 20 of hydrogenperoxide equivalent, in the presence of alcaline metal tungstate, in a 2-phase medium, at a temperature between 10° and 25° C.

4 Claims, No Drawings

PROCESS FOR PREPARING SULPHONYLPRISTINAMYCIN II$_B$

FIELD OF THE INVENTION

BACKGROUND OF THE INVENTION

26-[(2-Dialkylaminoalkyl)sulphonyl]-pristinamycins II$_B$ of general formula:

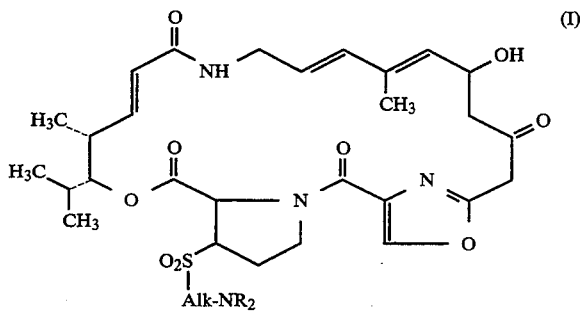

in which Alk represents a linear or branched alkylene radical and R represents linear or branched alkyl radicals, these radicals containing 1 to 10 carbon atoms, are products known for their antibacterial activity and their synergistic action on the antibacterial activity of pristinamycin I$_A$, as has been described in European Patent 191,662.

The pristinamycin II$_B$ derivatives of general formula (I) may be obtained by oxidation of the corresponding sulphide, in particular according to the teaching of European Patent 191,662, which describes the oxidation of a sulphide of general formula:

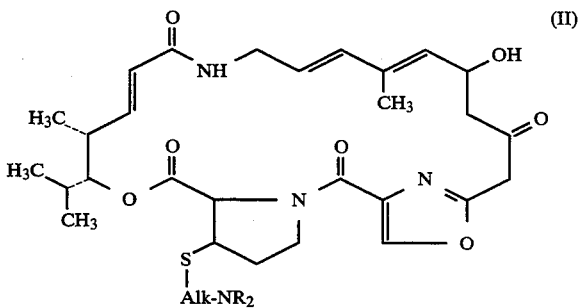

in which Alk and R are defined as above, with hydrogen peroxide in the presence of selenium dioxide. The reaction is performed in an aqueous or organic medium, in particular in an alcohol.

According to British Patent Application 2,206,577, the pristinamycin II$_B$ derivatives of general formula (I) may also be obtained by oxidation of the corresponding sulphide of general formula (II) with hydrogen peroxide in the presence of an alkali metal tungstate such as sodium tungstate, in an aqueous medium, for example acetone/water or acetonitrile/water or in a water-immiscible solvent such as a chlorinated hydrocarbon, at a temperature ranging from −5° C. to room temperature.

DESCRIPTION OF THE INVENTION

It has now been found that the oxidation reaction of the sulphide of general formula (II) leads to different oxidation products according to the conditions employed. It has, in effect, been demonstrated that the sulphone of pristinamycin II$_B$, of general formula (I), may be obtained in considerably improved yields by effecting oxidation of the sulphide of pristinamycin II$_B$ with 3.5 to 20 equivalents of hydrogen peroxide in the presence of an alkali metal tungstate such as, for example, sodium tungstate, in a two-phase medium, at a temperature of between 10° and 25° C.

It is necessary for the oxidizing agent to be introduced in large excess relative to the quantity of product to be oxidised and, for this purpose, for the proportion of oxidising agent/co-oxidizing agent to be maintained within certain limits. Hydrogen peroxide is employed in the proportion of 3.5 to 20 equivalents per mole of sulphide of pristinamycin II$_B$; the proportion of sodium tungstate generally varies from 5 to 0.5%.

The two-phase medium consists of a chlorinated solvent/water mixture such as, for example, a methylene chloride/water mixture or dichloroethane/water mixture or chloroform/water mixture.

It can also consist of a water/water-immiscible alcohol mixture such as, for example, an n-butanol/water mixture.

It is advantageous to work in a 50:50 (by volume) water/chlorinated solvent mixture, but it is also possible to vary these proportions.

The preferred catalyst is sodium tungstate, but it should be understood that the reaction may also be carried out in the presence of potassium tungstate.

The outcome of this novel implementation of the process of oxidation of 26-[(2-dialkylaminoalkyl)sulphonyl]pristinamycin II$_B$ is a very large improvement in yields as a result of the catalysis in a heterogeneous medium in the presence of predetermined relative quantities of oxidizing agent/co-oxidizing agent. According to the new process, yields of more than 70% can be achieved.

EXAMPLES

The examples which follow, given without implied limitation, illustrate the present invention.

EXAMPLE 1

A solution of 5 mg (0.0151 mmol; 1 mol%) of sodium tungstate in hydrogen peroxide (30%; 1.71 g; 15.1 mmol; 10 equivalents) is added in the course one minute at room temperature to a solution of 1 g (1.51 mmol) of 26-[(2-diethylaminoethyl)thio]-pristinamycin II$_B$ in 10 cm$^3$ of methylene chloride and 10 cm$^3$ of water. The reaction is slightly exothermic at the beginning. The reaction mixture is stirred for 16 hours at room temperature.

An assay of the reaction mixture reveals the following degree of conversion and yield:

| | |
|---|---|
| Degree of conversion = | 100% |
| True yield of sulphone = | 79% |

The organic phase is separated after settling has taken place and washed once with 20 cm$^3$ of water, then dried over sodium sulphate and concentrated to dryness. 26-[(2-Diethylaminoethyl)sulphonyl]-pristinamycin II$_B$ with an assay of 78% is thereby obtained (True yield =75%).

26-[(2-Diethylaminoethyl)thio]pristinamycin II$_b$ may be prepared as described in Patent EP 135,410.

EXAMPLE 2

Using the procedure described in Example 1, but replacing methylene chloride by 10 cm³ of 1,2-dichloroethane and stirring the reaction mixture for 4 hours 30 minutes, 26-[(2-diethylaminoethyl)sulphonyl]-pristinamycin II$_B$ with an assay of 71% is obtained (True yield = 70%).

EXAMPLE 3

1.25 g of sodium tungstate (3,789 mmol; 5 mol%) and then, in the course of 2 hours 30 minutes and at a temperature of 19°–20° C., 27.124 cm³ (265 mmol; 3.5 equivalents) of a solution of hydrogen peroxide (30%) in 73 cm³ of water are added successively to a solution of 52.966 g (75.88 mmol) of 26-[(2-diethylaminoethyl)-thio]pristinamycin II$_B$ in 500 cm³ of 1,2-dichloroethane and 427 cm³ of water. After stirring of the reaction mixture for a total of 8 hours 40 minutes, the following are obtained:

| degree of conversion = | 100% |
|---|---|
| true yield of 26-[(2-diethylamino-ethyl)sulphonyl]pristinamycin II$_B$ = | 78% |

The aqueous phase is separated after settling has taken place and extracted with twice 100 cm³ of 1,2-dichloroethane. The organic phases are combined and washed with 3 times 100 cm³ of water (until a non-oxidizing washing liquor is obtained) then dried over sodium sulphate. After filtration and concentration to dryness under reduced pressure, 52.91 g of a cream-white solid (weight yield = 100.9%) assaying at 74.3% of 26-[(2-diethyl-aminoethyl)sulphonyl]pristinamycin II$_B$, equivalent to a true yield of 75%, are obtained.

The sulphone thereby obtained may be converted to a di-p-toluoyltartrate by salification with di-p-toluoyltartaric acid. A salt assaying at 100% is obtained from this crude sulphone in an 82.6% yield. A total yield of 62% is thereby obtained for the oxidation followed by the salification.

EXAMPLE 4

Using the procedure described in Example 3, the oxidation of 1 g (1.51 mmol) of 26-[(2-diethyl-aminoethyl)thio]pristinamycin II$_B$ is carried out in 4 cm³ of 1,2-dichloroethane and 12 cm³ of water. After 5 hours' stirring, 26-[(2-diethylaminoethyl)sulphonyl]-pristinamycin II$_B$ is obtained in a true yield of 71%.

EXAMPLE 5

Working as in Example 3, the oxidation of 1 g (1.51 mmol) of 26-[(2-diethylaminoethyl)thio]pristinamycin II$_b$ in 16 cm³ of 1,2-dichloroethane and 4 cm³ of water produces, after 2 hours' stirring, 26-[(2-diethylaminoethyl)sulphonyl]pristinamycin II$_B$ in a true yield of 70%.

EXAMPLE 6

Working as in Example 3, the oxidation of 1 g (1.51 mmol) of 26-[(2-diethylaminoethyl)thio]pristinamycin II$_B$ in 10 cm³ of n-butanol and 10 cm³ of water produces, after 6 hours' stirring, 26-[(2-diethylaminoethyl)sulphonyl]pristinamycin II$_b$ in a true yield of 40%.

EXAMPLE 7

Working as in Example 3, 5 g (7.58 mmol) of 26-[(2-diethylaminoethyl)thio]pristinamycin II$_B$ are oxidized in 50 cm³ of water and 50 cm³ of 1,2-dichloroethane with 25 mg (0.0758 mmol; 1 mol %) of sodium tungstate dihydrate and 8.59 g (7.58 mmol; 10 eq.) of 30% hydrogen peroxide in the course of 4 hours 30 minutes at between 19° and 23° C. After treatment, 5.18 g of 26-[(2-diethylaminoethyl)sulphonyl]pristinamycin II$_B$ assaying at 74%, equivalent to a true yield of 73%, are obtained.

EXAMPLE 8

Working as in Example 3, 1 g (1.51 mmol) of 26-[(2-diethylaminoethyl)thio]pristinamycin II$_b$ is oxidized with 5 mg (0.015 mmol; 1 mol %) of sodium tungstate dihydrate and 0.855 g (7.55 mmol; 5 eq.) of hydrogen peroxide in the course of 8 hours at between 20° and 24° C. to produce the corresponding sulphone in a 77% yield.

EXAMPLE 9

Working as in Example 8, 1 g (1.51 mmol) of 26-[(2-diethylaminoethyl)thio]pristinamycin II$_B$ is oxidized in the course of 1 hour 30 minutes at 20° C. with 25 mg (0.0755 mmol; 5 mol %) of sodium tungstate dihydrate and 1.71 g (1.51 mmol; 10 eq.) of 30 % hydrogen peroxide to 26-[(2-diethylaminoethyl)sulphonyl]pristinamycin II$_B$ in a 75% yield.

EXAMPLE 10

Working as in Example 8, the oxidation of 26-[(2-diethylaminoethyl)thio]pristinamycin II$_B$ carried out at 20° C. in the presence of 2.5 mg (0.0075 mmol; 0.5 mol %) of sodium tungstate and 1.71 g (1.51 mmol; 10 eq.) of 30 % hydrogen peroxide produces, in the course of 6 hours, 26-[(2-diethylaminoethyl)sulphonyl]pristinamycin II$_b$ in a 69% yield.

EXAMPLE 11

Working as in Example 10, the oxidation of 26-[(2-diethylaminoethyl)thio]pristinamycin II$_B$ performed with 3.42 g (30.2 mmol; 20 eq.) of 30 % hydrogen peroxide produces, in the course of 6 hours, 26-[(2-diethylaminoethyl)sulphonyl]pristinamycin II$_B$ in a 66% yield.

EXAMPLE 12

Working as in Example 7 on 1 g (1.51 mmol) of 26-[(2-diethylaminoethyl)thio]pristinamycin II$_B$ in 10 cm³ of chloroform instead of 1,2-dichloroethane, 26-[(2-diethylaminoethyl)sulphonyl]pristinamycin II$_B$ is obtained in a 72% yield in the course of 15 hours.

I claim:

1. A process for preparing 26-[(2-dialkylaminoalkyl)-sulphonyl]pristinamycin II$_B$ of formula:

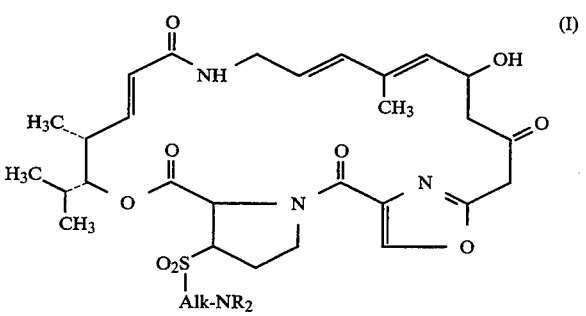

(I)

in which Alk represents a linear or branched alkylene radical and R represents linear or branched alkyl radicals, these radicals containing 1 to 10 carbon atoms, comprising oxidation of 26-[(2-dialkylaminoalkyl)thio]-pristinamycin II$_B$ of formula:

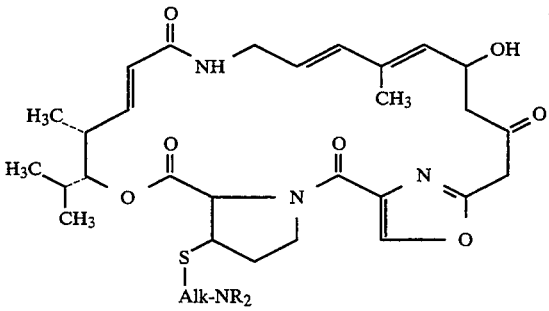

in which Alk and R are defined as above, with 3.5 to 20 equivalents of hydrogen peroxide in the presence of an alkali metal tungstate, in a two-phase medium, at a temperature of between 10° and 25° C.

2. A process according to claim 1, wherein the alkali metal tungstate is sodium tungstate.

3. A process according to claim 1, wherein the alkali metal tungstate is introduced in the proportion of 5 to 0.5 mol%.

4. A process according to claim 1, wherein the two-phase medium consists of a water/chlorinated solvent or water/n-butanol mixture.

* * * * *